(12) United States Patent
Bakhtiari et al.

(10) Patent No.: US 8,686,362 B2
(45) Date of Patent: Apr. 1, 2014

(54) MILLIMETER WAVE SENSOR FOR FAR-FIELD STANDOFF VIBROMETRY

(75) Inventors: Sasan Bakhtiari, Darien, IL (US); Nachappa Gopalsami, Naperville, IL (US); Thomas W. Elmer, Westmont, IL (US); Apostolos C. Raptis, Downers Grove, IL (US)

(73) Assignee: UChicago Argonne, LLC, Chicago, IL (US)

( * ) Notice: Subject to any disclaimer, the term of this patent is extended or adjusted under 35 U.S.C. 154(b) by 767 days.

(21) Appl. No.: 12/770,438

(22) Filed: Apr. 29, 2010

(65) Prior Publication Data

US 2010/0290063 A1    Nov. 18, 2010

Related U.S. Application Data

(60) Provisional application No. 61/174,818, filed on May 1, 2009.

(51) Int. Cl.
*G01J 5/00*    (2006.01)
(52) U.S. Cl.
USPC ........................................................ 250/338.1
(58) Field of Classification Search
USPC ........................................................ 250/338.1
See application file for complete search history.

(56) References Cited

U.S. PATENT DOCUMENTS 5,468,964 A    11/1995    Gopalsami et al.
5,886,534 A *    3/1999    Bakhtiari et al. ............. 324/642
7,495,218 B2    2/2009    Gopalsami et al.
2008/0119716 A1*    5/2008    Boric-Lubecke et al. ..... 600/407
2010/0204587 A1*    8/2010    Lin et al. ........................ 600/484

OTHER PUBLICATIONS

Chen et al. "Microwave Life-Detection Systems for Searching Human Subjects Under Earthquake Rubble or Behind Barrier", IEEE Transactions on Biomedical Engineering, vol. 27, No. 1, 2000.*
S. Bakhtiari and R. Zoughi, "*A Model for Backscattering Characteristics of Tall Prairie Grass Canopies at Microwave Frequencies: A Theoretical Approach*," Remote Sensing of Environment, vol. 36, No. 2, pp. 137-147, May 1991.
S. Bakhtiari, S. Ganchev and R. Zoughi, "Open-Ended Rectangular Waveguide for Nondestructive Thickness Measurement and Variation Detection of Lossy Dielectric Slabs Backed by a Conducting Plate," *IEEE* Transactions on Instrumentation and Measurement, vol. 42, No. 1, pp. 19-24, Feb. 1993.

(Continued)

*Primary Examiner* — David Porta
*Assistant Examiner* — Edwin Gunberg
(74) *Attorney, Agent, or Firm* — Foley & Lardner

(57) ABSTRACT

A millimeter wavelength (MMW) measurement system for remote detection of object characteristics and methods for detecting such characteristics. The MMW measurement system comprises a front-end and an optional signal conditioning component. The MMW front-end includes an oscillator, a transceiver portion, and an antenna for focusing a detection component comprising micrometer level wavelength electromagnetic radiation onto the object. A portion of the electromagnetic radiation reflected by the object is received by the MMW measurement system, which is indicative of a displacement of the object. The MMW system may be configured to detect micrometer level displacement of the object disposed tens of meters from the MMW measurement system. In various embodiments the object may be a natural object, including a human, and the displacement may be indicative of a heart rate and/or a respiratory function.

19 Claims, 13 Drawing Sheets

(56) References Cited

OTHER PUBLICATIONS

S. Bakhtiari, N. Qaddoumi, S. Ganchev and R. Zoughi, "*Microwave Non-Contact Examination of Disbond and Thickness Variation in Stratified Composite Media*," IEEE Trans. on Microwave Theory and Tech., vol. 42, No. 3, Mar. 1994.

S. Bakhtiari, S. Ganchev and R. Zoughi, "*Analysis of Radiation of an Open-Ended Coaxial Line into Stratified Dielectrics*," IEEE Trans. on Microwave Theory and Tech., vol. 42, No. 7, Jul. 1994.

N. Gopalsami, D. B. Kanereykin, V.D. Asanov, S. Bakhtiari, and A.C. Raptis, "*Microwave Radar Detection of Gas Pipeline Leaks*," Proc. of the 29th Rev. of Prog. In Quantitative Nondestruction Evaluation, Bellingham, WA, Jul. 14-19, 2002.

N. Gopalsami, and A.C. Raptis, "Millimeter-Wave Radar Sensing of Airborne Chemicals," *IEEE Trans. Microwave Theory Techniques*, vol. 49, pp. 646-653, 2001.

N. Gopalsami, S. Bakhtiari, A.C. Raptis, S. L. Dieckman, and F.C. De Lucia, "Millimeter Wave Measurements of Molecular Spectra with Application to Environmental Monitoring," *IEEE Transactions on Instrumentation and Meaurement*, vol. 45, pp. 225-230, 1996.

N. Gopalsami, A.C. Raptis and J. Meier, "Millimeter-Wave Cavity Ringdown Spectroscopy," *Review of Scientific Instruments*, pp. 259-262, 2002.

N. Gopalsami, S. Bakhtiari, T. Elmer and A.C. Raptis, "*Remote Detection of Chemicals with Passive Millimeter Waves*," SPIE vol. 6378, pp. 6378A 1-12, 2006.

N. Gopalsami, S. Bakhtiari, T. Elmer and A.C. Raptis, "Millimeter Wave Sensor for Far-Field Standoff Vibrometry," *Review of Quantative Nondestructive Evaluation*, vol. 28, p. 1641-1648, 2009.

"Imaging Technology", Innovation & Technology, Transportation Security Administration, Apr. 11, 2010, 5 pages, http://www.tsa.gov/approach/tech/imaging_technology.htm.

"Millimeter Wave Scanner", Wikipedia, the Free Encyclopedia, Apr. 11, 2010, 5 pages, http://en.wikipedia.org/wiki/Millimeter_wave_scanner.

\* cited by examiner

MILLIMETER WAVE SENSOR FOR FAR-FIELD STANDOFF VIBROMETRY

CROSS REFERENCE TO RELATED APPLICATIONS

This application is related to and claims priority from U.S. Provisional Patent Application 61/174,818, filed May 1, 2009 and is hereby incorporated by reference in its entirety.

STATEMENT OF GOVERNMENT INTEREST

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

FIELD OF THE INVENTION

The present invention relates generally to the field of remote detection measurement systems. More particularly, the present invention relates to measurement systems capable of far-field detection of various characteristics of natural and man-made objects.

BACKGROUND OF THE INVENTION

This section is intended to provide a background or context to the invention that is, inter alia, recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Electromechanical and optical sensors have been used in the past for monitoring various object characteristics, including vibration associated with industrial machinery and minute displacements of man-made structures. Examples include strain gauges for measuring deformation; accelerometers for measuring vibration, acceleration, velocity and displacement; and laser-based systems that sense the displacement of optically reflective targets. Such devices, although often accurate, require the sensor to be either in direct contact or at close proximity to the object under test.

Optical sensors on the other hand generally require optically reflective surfaces and precise alignment. For non-contact standoff monitoring applications, the current state-of-the-art is almost exclusively based on laser Doppler vibrometry/velocimetry (heterodyne interferometer) that can measure subtle surface motions collinear with the sensor's line-of-sight. The signal-to-noise-ratio (S/N) of an optical sensor is proportional to the square root of the reflected signal from the surface of a target. With most natural and man-made structures having optically rough surfaces, photon scattering often results in little signal being reflected back to the sensor and thus limits the range and sensitivity of optical systems. In addition, optical signals are strongly affected by a wide range of ambient circumstances including atmospheric conditions such as weather, target composition and measurement configuration, for example, incidence angle and line-of-sight accessibility.

With regard to the measurement of natural objects, the ability of microwave energy to penetrate through clothing with little attenuation and its reflection off of human skin has been exploited to detect concealed objects. For example, radar techniques have been attempted for remote detection of human vital signs. However, these tests have been performed at the microwave or lower range of the millimeter-wave band and thus lack certain of the advantages of a millimeter wave measurement system.

The longer electromagnetic wavelengths of millimeter-wave (MMW) techniques can be harnessed to overcome certain limitations associated with conventional optical sensors. Active and passive MMW techniques have been attempted in the past for various remote sensing applications. Millimeter wave techniques have also been used for nondestructive examination of materials, but at close standoff distances.

SUMMARY OF THE INVENTION

It is desirable to overcome the limitations of conventional remote (non-contact) measurement systems and provide a measurement system capable of far-field detection and/or monitoring of various characteristics of manmade objects, for example, a machine, structure, or industrial facility. There is also a need for a measurement system that is capable of detecting and/or monitoring characteristics such as biometric activity of natural objects, for example, a human or animal. There is a further need to provide measurement systems in these areas that are relatively insensitive to surface properties of the target and the arrangement between the measurement system and the target, while capable of operating under various non-ideal ambient conditions.

In situations where placement of a sensor or reflector on the target is not feasible, microwave interferometric and radar techniques may be the only viable method for standoff monitoring of subtle vibrations. Phase interference of coherent microwave radiation can be used to measure displacement and velocity. At millimeter-wave frequencies, displacement can be measured with micron level resolution using either continuous wave or swept-frequency techniques. Pulsed techniques may be employed to acquire similar information at larger distances. The primary technical challenge with such systems is to deduce the relevant information about the target and eliminate all irrelevant but typically wide-band interfering signals.

Characteristic acoustic signals that may be received from a structure and/or its surrounding objects may be correlated with the operation of a device or plant or the health condition of a structure. A MMW counterpart of an optical vibrometer was developed for such applications. In view of the tradeoff between sensitivity and range, it is expected that millimeter wavelengths, which occupy the band between microwaves and far-infrared frequencies, will provide the optimum operating frequency within the microwave band.

The MMW measurement system of the present invention may be applied, in among other uses, to far-field monitoring of industrial facilities, the condition of machinery and structures. For example, the system may be used to detect the operation of machinery within a building by measuring the vibrations of the external surfaces of the building caused by the operating machinery. The MMW measurement system may also be used for nondestructive testing of structures and components and non-contact sensing of defects in metals and composite materials. Still further, the MMW measurement system is applicable to biometric sensing for health, medical and national security applications. A MMW measurement system of relatively small size and low-power may be constructed that is suitable for portable operation.

One embodiment of the invention relates to a MMW system comprising a front-end and a signal conditioning component that may optionally route the acquired signal to a data acquisition system and/or computer for further processing, analysis and storage. The MMW front-end includes a Gunn diode oscillator, a modulator/regulator coupled to the oscillator for a power supply, an isolator, a directional coupler, a circulator, a quadrature mixer, and a lens antenna. The transmitter portion of the MMW front-end may optionally include a heater to improve frequency stability. The transceiver portion of the MMW front-end includes a homodyne configuration for down-conversion of the modulated carrier signal to an acoustic frequency range that is detected by the quadrature mixer. In a particular embodiment, the optical lens antenna comprises a Gaussian optic lens.

In addition to the MMW sensor front end, data acquisition and analysis hardware and software may by used to help detect and isolate faint signal returns in the presence of relatively strong interference from background noise. Various frequency and time domain filtering schemes may be applied for both on-line and off-line processing of data received from the MMW measurement system.

These and other advantages and features of the invention, together with the organization and manner of operation thereof, will become apparent from the following detailed description when taken in conjunction with the accompanying drawings, wherein like elements have like numerals throughout the several drawings described below.

DETAILED DESCRIPTION OF VARIOUS EMBODIMENTS

Figure 1:
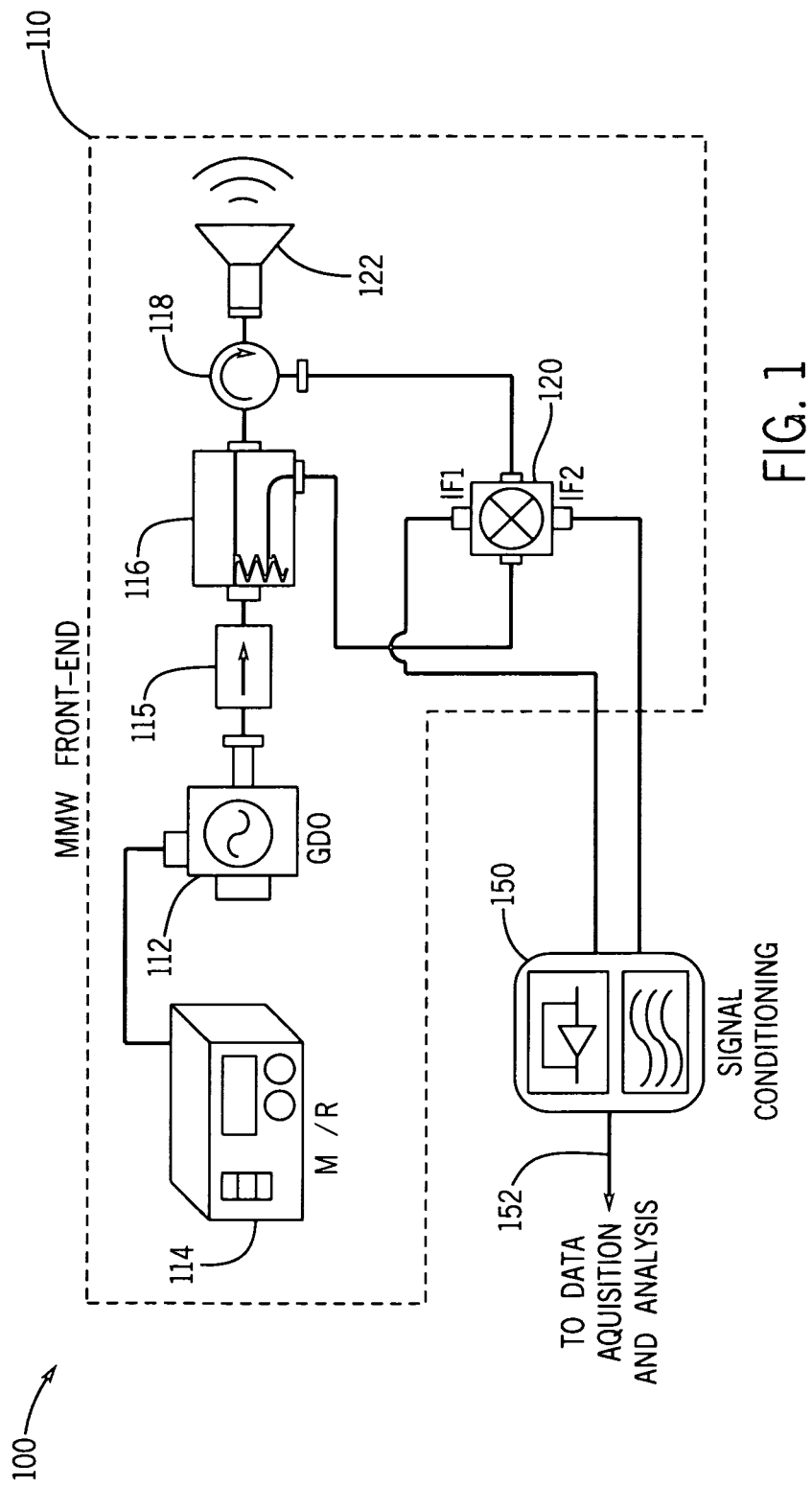
FIG. 1 shows a schematic of a MMW measurement system according to an embodiment of the present invention.

A millimeter-wave (MMW) measurement system has been developed for remote detection of vibrations associated with natural objects and man-made structures at far-field standoff distances. The MMW measurement system can measure object characteristics, e.g., displacement, from a distance by sensing remote acoustic vibrations at or near the object using high-frequency electromagnetic (EM) waves. Displacements on the order of fractions of a millimeter may be accurately measured from a distance of tens of meters and even hundreds of meters separating the object and the measurement system sensor. Indeed, millimeter-wave frequencies are capable of measuring displacement with sub-micron resolution using a continuous wave or swept-frequency approach. Pulsed wave techniques can be applied to obtain longer standoff distances.

A solid-state Gunn and Impact Avalanche Transit Time (IMPATT) source that can produce up to tens of milliwatts of power can be used in combination with highly sensitive solidstate detectors and low-noise amplifiers to develop compact, low input power sensors that can transmit and receive signals over far-field distances. Because the measurement accuracy is dependent on the operating wavelength, higher frequencies will provide more accurate information about the target under interrogation. At microwave frequencies, acoustically induced vibrations can be measured with sub-millimeter accuracy using interferometric methods. Similar systems operating at millimeter wavelengths can provide one to two orders of magnitude improvement in dynamic range. While the operation of a MMW measurement system is analogous to its lower-frequency counterparts, higher frequency MMW systems are inherently smaller in size and thus more desirable for portable or clandestine operations.

Measurements from the MMW measurement system are acquired using Doppler frequency shift or phase modulation induced in a monochromatic EM signal reflected from the target surface may be used for far-field measurement. In one embodiment, the MMW system of the present invention comprises a relatively compact W-band system that employs solid-state active and passive components to capture target displacement and may be used to obtain other targets characteristics, e.g., position, velocity, acceleration, mode, etc, based on the change in displacement.

Acoustic vibrations of structures or reverberations from a nearby object (e.g., structural as well as seismic vibrations) may be detected by measuring the modulation induced in a coherent signal reflected from the object's surface. Analogous to heterodyne detection of interferometric optical signals, mixing of the backscattered electromagnetic signal with a portion of the reference transmitted signal (i.e., a local oscillator) allows recovery of low-frequency modulations induced by the vibrating target. Thus, phase interference of the coherent MMW radiation is used to deduce information about relative small in-plane displacements. In-plane displacements may be sensed by either measuring the Doppler frequency shift or the phase modulation induced by the target on the backscattered carrier signal. In their basic form, these effects may be expressed as:

$$f_d(t) = \frac{2v}{\lambda}\cos(\omega_{vib}t + \phi) \qquad \text{Eq. 1}$$

and $$\varphi(t) = \frac{4\pi}{\lambda}d(t) \qquad \text{Eq. 2}$$

in which $\lambda$ is the carrier wavelength, $v$ is the target velocity, $\omega_{vib}$ is the vibration angular frequency, $\phi$ is the angle between the direction of target motion and the beam, and $d$ is the target displacement. In reference to Eq. (2) above, phase interference of coherent MMW radiation acquired over a period of time may be used to remotely obtain information about displacement and in turn the vibrational frequency of an object.

According to one embodiment of the present invention, the MMW measurement system comprises an interferometer with an MMW sensor front-end capable of remotely detecting acoustically induced modulations. As shown in FIG. 1, the MMW measurement system 100 comprises an MMW front-end 110 and a signal conditioning component 150. The signal conditioning component 150 may include an output 152 configured to couple to a data acquisition and or analysis component.

The MMW front-end 110 may comprise a Gunn diode oscillator (GDO) 112, a modulator/regulator 114 coupled to the GDO 112, an isolator 115, a directional coupler 116, a circulator 118, a quadrature mixer 120, and an optic lens antenna 122. The transmitter portion of the MMW front-end may further include a heater (not shown) to improve frequency stability. In one preferred embodiment, the GDO 112 comprises a W-band (94 GHz) solid-state GDO that uses a 5 V modulator-regulator as its power supply that allows frequency or amplitude modulation of the source.

In another embodiment, the transceiver portion of the MMW front-end 110 comprises a homodyne configuration for down-conversion of the modulated carrier signal to an acoustic frequency range that is detected by the quadrature mixer 120. The quadrature mixer 120 simultaneously obtains both the amplitude and the phase information from the MMW front-end 110. In a particular embodiment, the optic lens antenna 122 comprises a six inch Gaussian optic lens antenna configured to focus the beam on a target to be measured. The optic lens may be mounted to, for example, a telescope for alignment in relation to the target. The signal conditioning component 150 may include a plurality of tunable bandpass filters and low-noise amplifiers configurable to enhance the signal obtained from the MMW front-end 110.

Figure 2A:
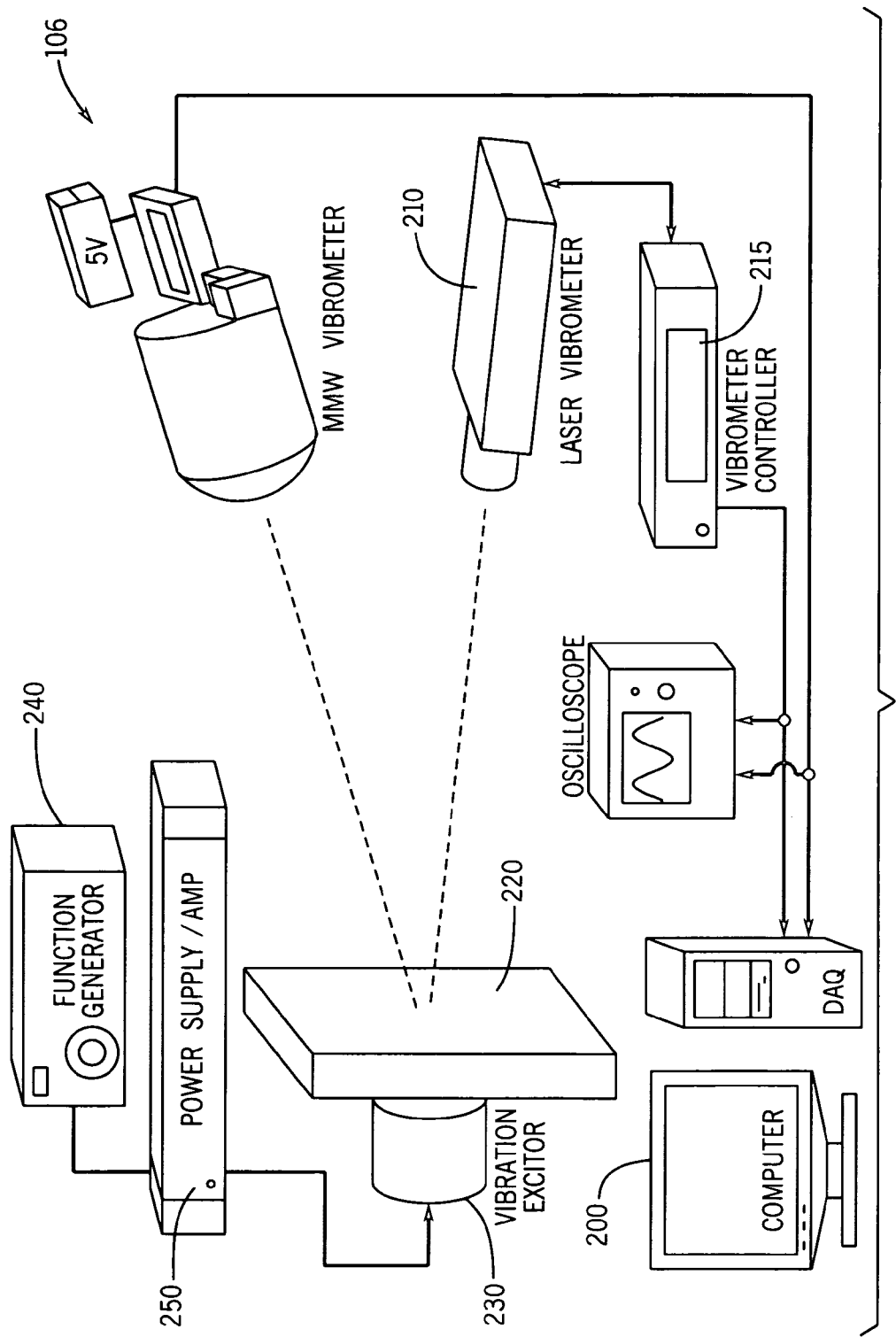
FIG. 2A shows a schematic of an apparatus used for evaluation of remote detection of acoustic vibrations with the MMW measurement system of FIG. 1.

Data acquisition and analysis from the MMW system 100 may be carried out by a computer-based hardware and/or software system 200 shown in FIG. 2A coupled to the output 152. For example, a four channel, 24-bit data acquisition board may be employed for signal acquisition and A/D conversion. In a particular embodiment, LabVIEW™ software, for example, operating on a computer may be used to carry out all data acquisition operations. The configuration of the present system permits both off-line and substantially real time acquisition and analysis of MMW obtained data. It should be noted that other software, hardware and combinations thereof may be employed for data acquisition and analysis.

Figure 2B:
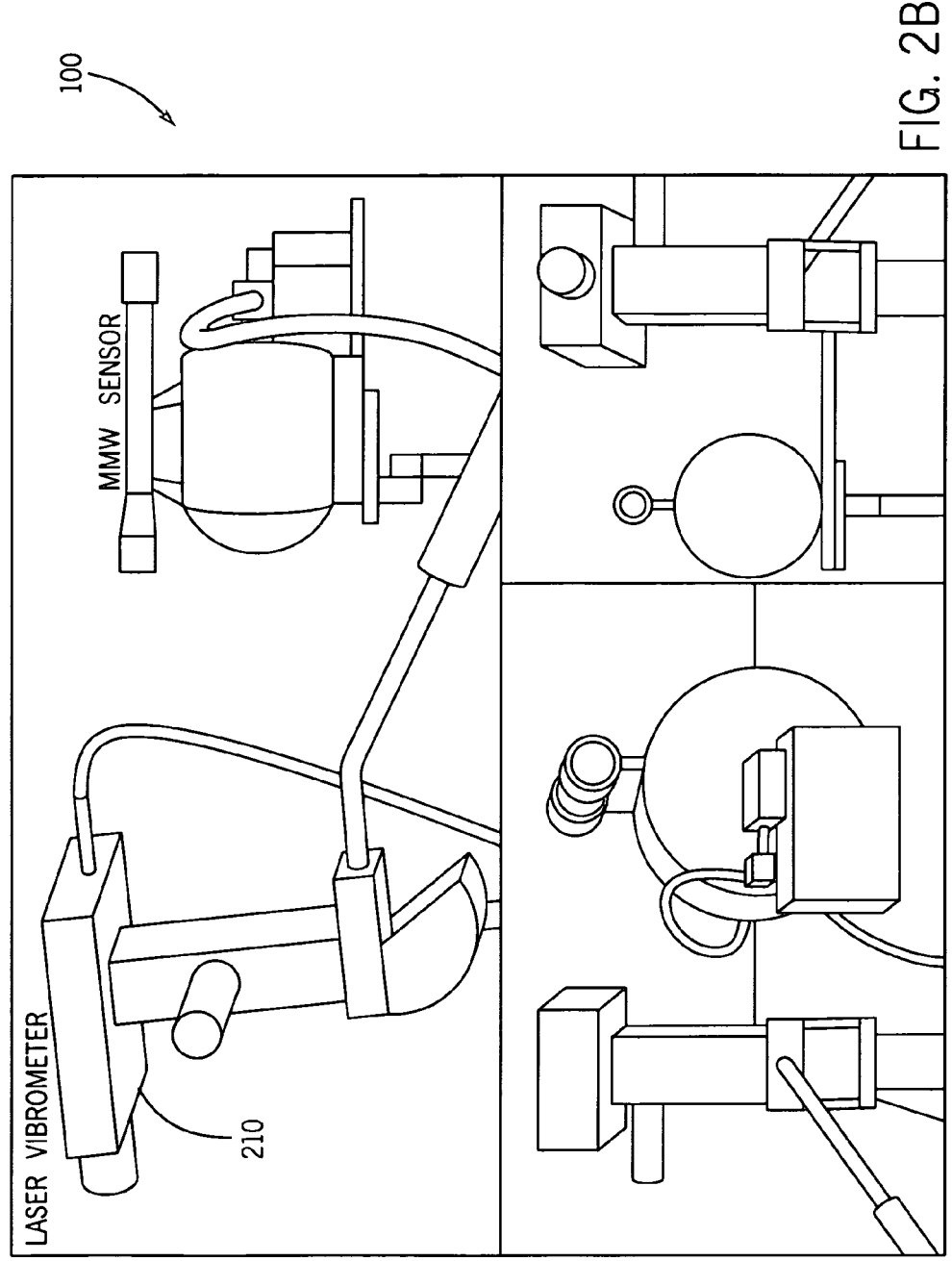
FIG. 2B shows an image of a laboratory setup showing (top) a laser vibrometer and an MMW sensor, and (bottom) a front view and a back view of the laser vibrometer and the MMW sensor and a target (white square)

FIGS. 2A and 2B show a laboratory setup of an embodiment of the MMW system 100. A commercial optical vibrometer 210 (class-II helium neon laser) and controller 215 that were used to verify the performance of the MMW system 100 is also visible. Further visible in FIG. 2B (background) is a target structure 220 comprising a cinder block attached to a vibration exciter 230 to simulate multimode excitation of a target. The cinder block, with a porous surface, was chosen because it represents a typical surface condition of building materials. An arbitrary function generator 240 in conjunction with a power amplifier 250 provided the input to the vibration exciter 230.

In the laboratory setup described above, a LabVIEW™ virtual instrument (VI) was implemented to allow multi-channel recording and real-time processing and visualization of the sensor output. However, other software, hardware and combinations thereof may be implemented. The VI was configured to deliver one-dimensional time traces and various signal processing to provide, for example, power spectrum and two-dimensional time-frequency image displays. A graphical user interface (GUI) was also developed in the MATLAB environment for post processing of recorded data. The GUI is implemented in a modular fashion and allows for convenient update of the existing functions (e.g., filters) or to create and interface new aspects in the GUI, independent of the source code.

For example, various signal processing filters may be employed in the data processing system for time and/or frequency domain filtering to enhance the signal to noise ratio (S/N) of the acquired data, including peak detection, smoothing and band pass filtering. These techniques may be used to identify, isolate and characterize faint signal returns in the presence of relative strong interference and background noise. Still further, various statistical techniques may be applied to enhance data processing and/or analysis. Again, these techniques may be applied in a near real-time configuration to obtain substantially immediate information about a target, or off-line. The near-real time configuration may be advantageously incorporated into a portable MMW measurement system that may employed in various contexts, including emergency, national security, industrial and remote monitoring applications.

Representative data from comparative studies demonstrate substantial advantages of the MMW system over a conventional laser vibrometer with regard to detection range, ease of alignment, and reduced sensitivity to surface condition of the target—important criteria for many field applications. For instance, while the laser beam in all test cases had to be pointed directly at the optical reflector placed on the vibrating plate, the MMW signal could be detected from any arbitrary location on the target and from a wide range of view angles. Sensitivity studies demonstrate that the ability of this low power MMW system to resolve displacements of a few micrometers from standoff distances of tens of meters. A further increase in range of the MMW sensor can be achieved through either hardware and/or software modifications. These include employment of solid-state sources with higher output power, incorporation of a low-noise amplifier in the sensor front-end, and more elaborate signal processing and data analysis.

Additionally, as a consequence of operation at longer electromagnetic wavelengths, MMW radiation can penetrate through many optically opaque materials and efficiently reflect off of optically coarse surfaces. Because of their shorter wavelengths, millimeter waves can provide improved sensitivity over microwave techniques for detection of subtle displacements associated with human vital signs. In particular, the MMW measurement system can be applicable to the remote monitoring of human vital signs. For example, as described in detail below, tests demonstrate the ability of the MMW system to detect displacements associated with the respiration and heartbeat of a human subject at a distance of tens of meters from the subject. Thus, the MMW system is expected to have a wide range of applications in the biomedical as well as in the homeland security area. The MMW system can also be applicable to other human and animal monitoring applications and still other applications, involving monitoring and characterization of various man-made structures.

The MMW system of the present invention is capable of operating under various conditions, including day or night, unfavorable weather and wide temperature fluctuations. Further, the MMW system is surprisingly insensitive to measurement conditions such as distance, incidence angle, surface condition, compared to conventional measurement systems such as laser vibrometry. Thus, the MMW system will be easier to use and more capable in obtaining reliable measurement information, relative to conventional measurements systems like laser vibrometry. In addition, to the flexibility of the MMW system, the MMW system also offers at least equivalent sensitivity compared to conventional systems at short to moderate ranges, while it provides greatly enhanced sensitivity at longer ranges.

Various aspects of the present invention will now be further explained in the following illustrative examples. However, the present invention should not be construed as limited thereby. One of ordinary skill in the art will understand how to vary the exemplified systems and methods to obtain the desired results. The following nonlimiting examples are illustrative of various aspects of the invention.

Example 1

Figure 3A:
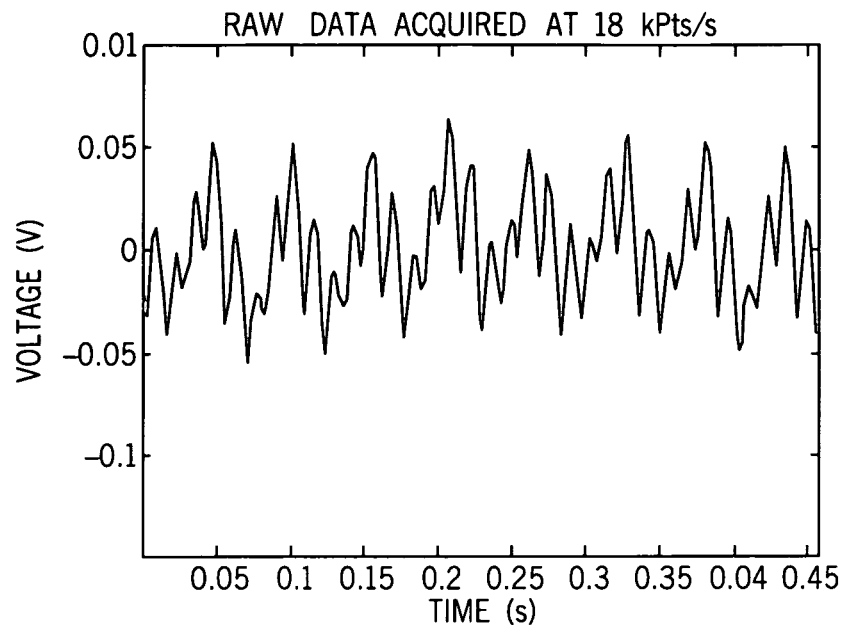
FIG. 3A shows a time trace plot of data obtained from the MMW system collected from a multimode vibrating target excited at two frequencies.
Figure 3B:
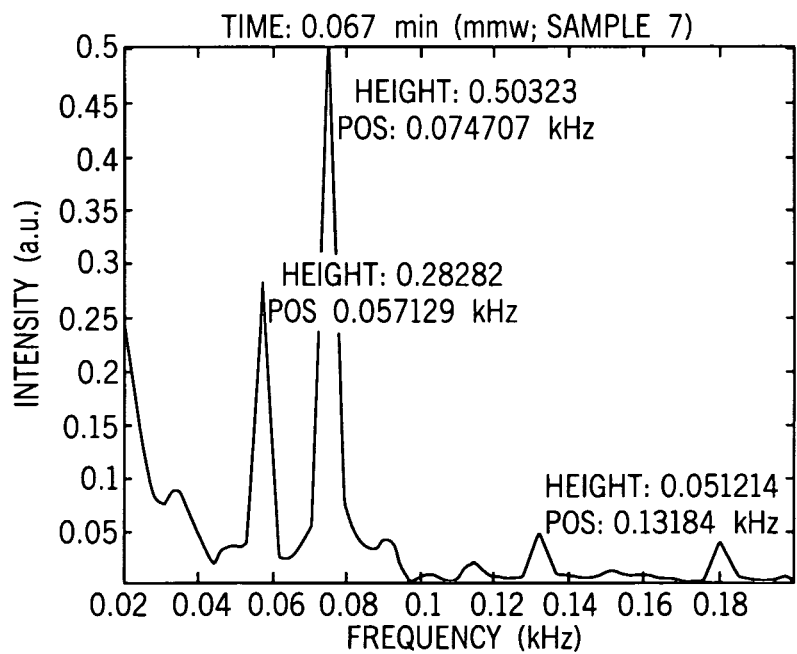
FIG. 3B shows a power spectrum plot of the time data of FIG. 3A.
Figure 3C:
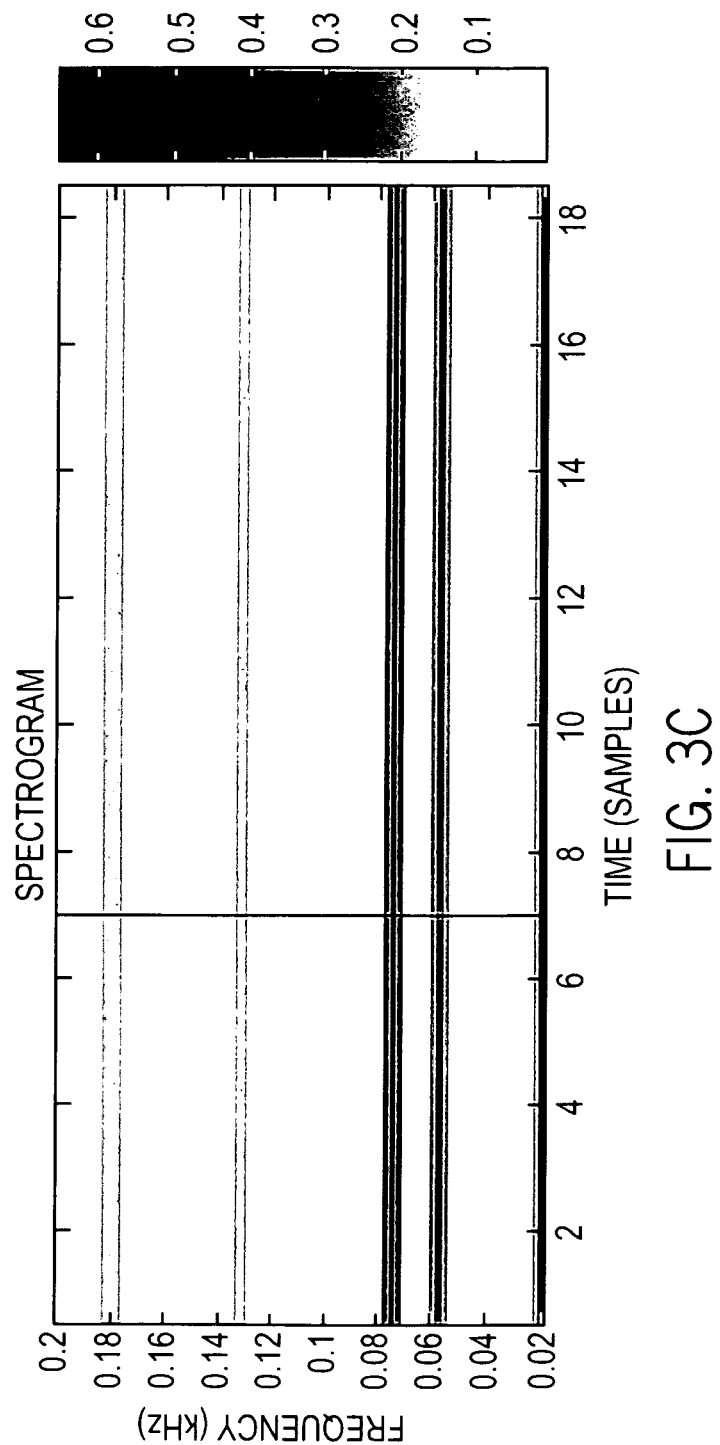
FIG. 3C shows a frequency-time plot (spectrogram) of the temporal data of FIG. 3B.
Figure 4A:
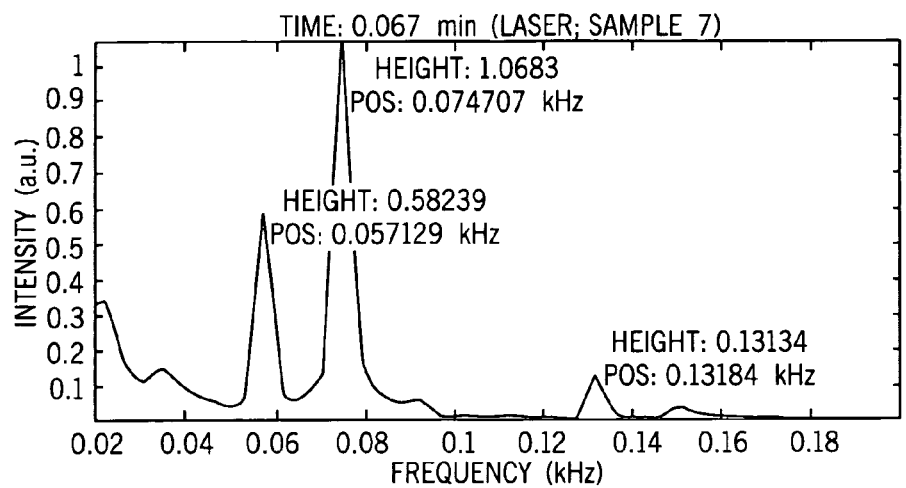
FIGS. 4A and 4B show frequency plots obtained from the laser vibrometer and the MMW system, respectively, of a target under multimode vibration at a range of about 15 m.
Figure 4B:
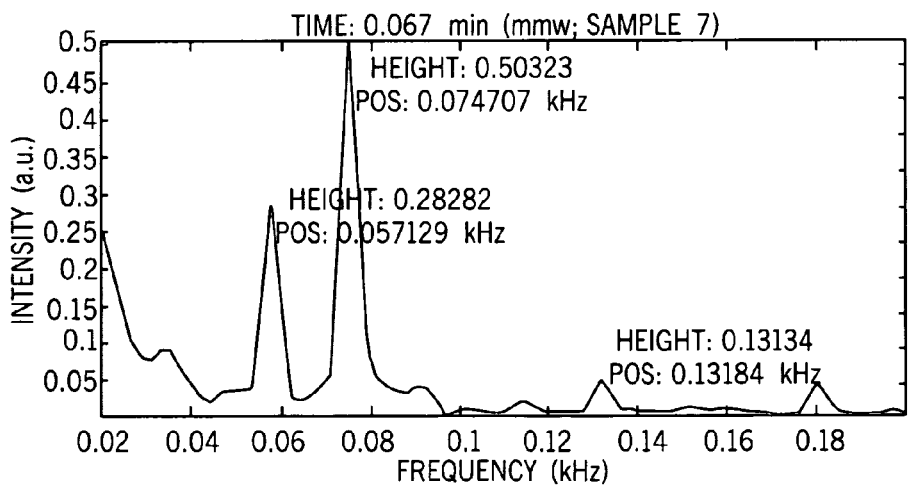

For preliminary evaluation, the target was excited with a composite periodic signal simulating two modes of vibration. To verify the MMW system readings, the output of the laser vibrometer was simultaneously recorded on a separate channel. FIGS. 3A-3C show a typical display of data in the main GUI window collected with the MMW system. Expanded display of the power spectral density plots for both the MMW system and the laser vibrometer system are shown in FIGS. 4A and 4B, respectively. For the short standoff distance of about 15 m in this case, the data indicate excellent agreement between the output of the laser vibrometer system and the MMW system. It is should be noted that for all the test cases the laser beam of the laser vibrometer was aimed at the center of the vibrating target that was fitted with an optically smooth reflector to obtain maximum signal return. On the other hand, the MMW beam was aimed at an arbitrary location away from the center of the target.

Example 2

Figure 5A:
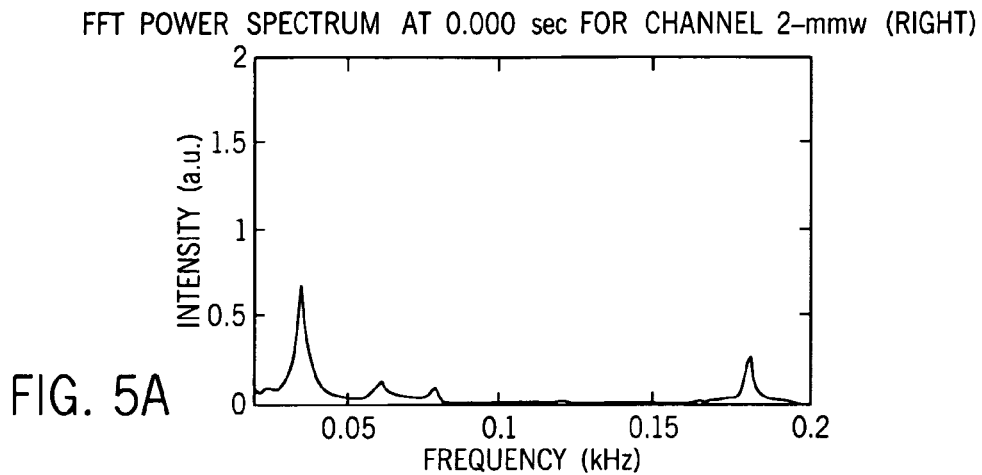
FIGS. 5A-5C show frequency plots obtained from the MMW system taken at three locations on the target and depicting the primary vibration modes of the target.
Figure 5B:
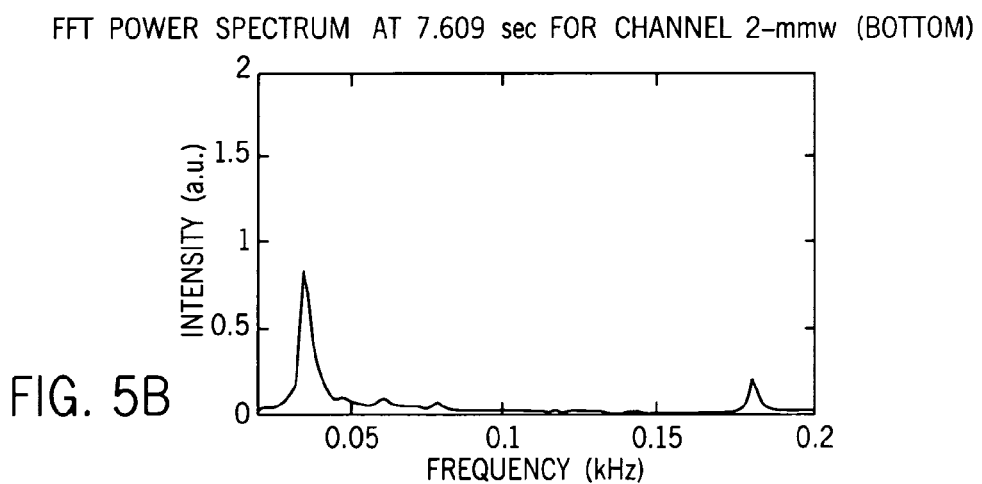
Figure 5C:
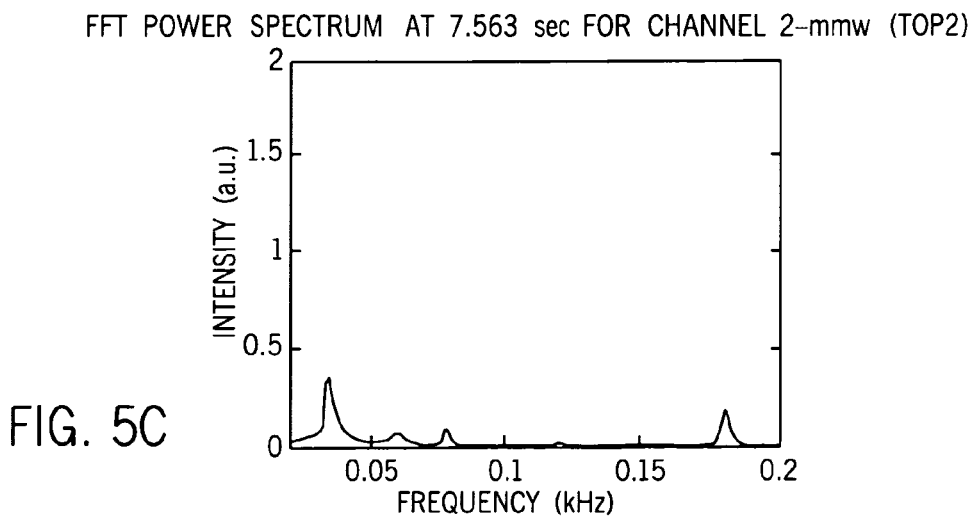

Additional tests were carried out to assess the effect of the surface condition of the target (reflectivity) on detection. FIGS. 5A-5C depict data collected from the MMW system obtained from three different locations on the target's surface. In these tests, the reflector disposed at the center of the target was covered with radar absorbing foam. As seen from the Figures, the MMW system detected a clear signal indicative of the primary modes of vibration for all three locations. The measurements were relatively insensitive to diffuse scattering from the optically rough surfaces. Thus, the MMW system does not require precise alignment and may be aimed at any arbitrary location on the target.

Example 3

Figure 6A:
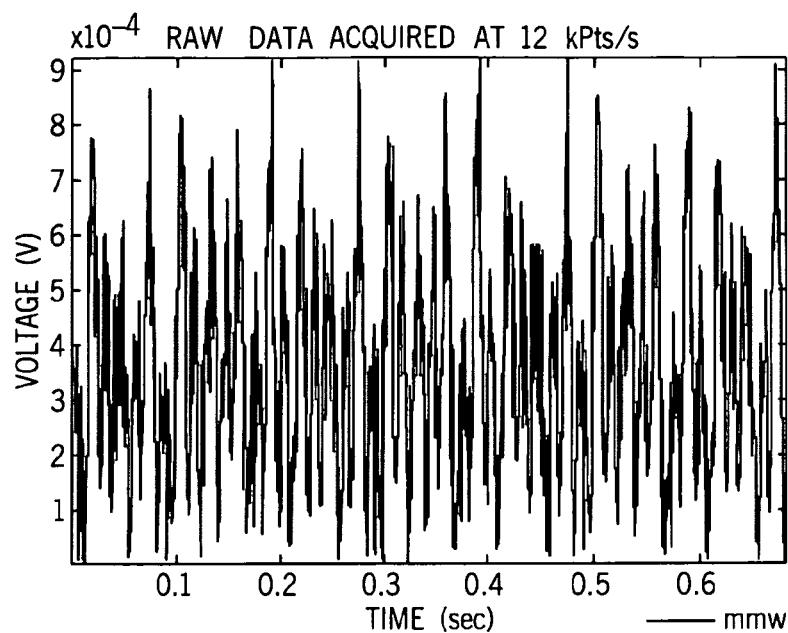
FIG. 6A shows a time trace plot.
Figure 6B:
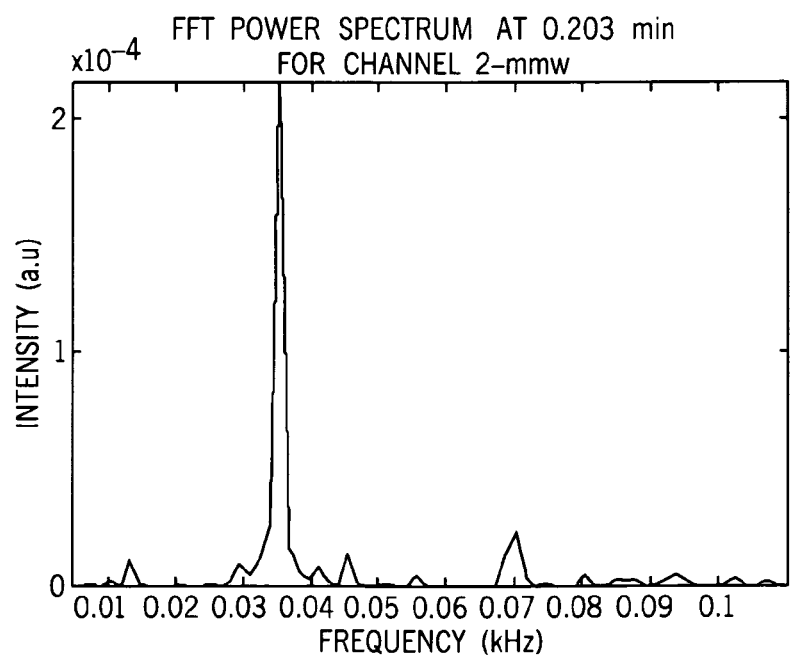
FIG. 6B shows a power spectrum and FIG. 6C shows a frequency-time display (bottom)) obtained from the MMW measurement system at a range of about 25 m with oblique incidence (<10°) from single mode excitation (35 Hz) of the target.
Figure 6C:
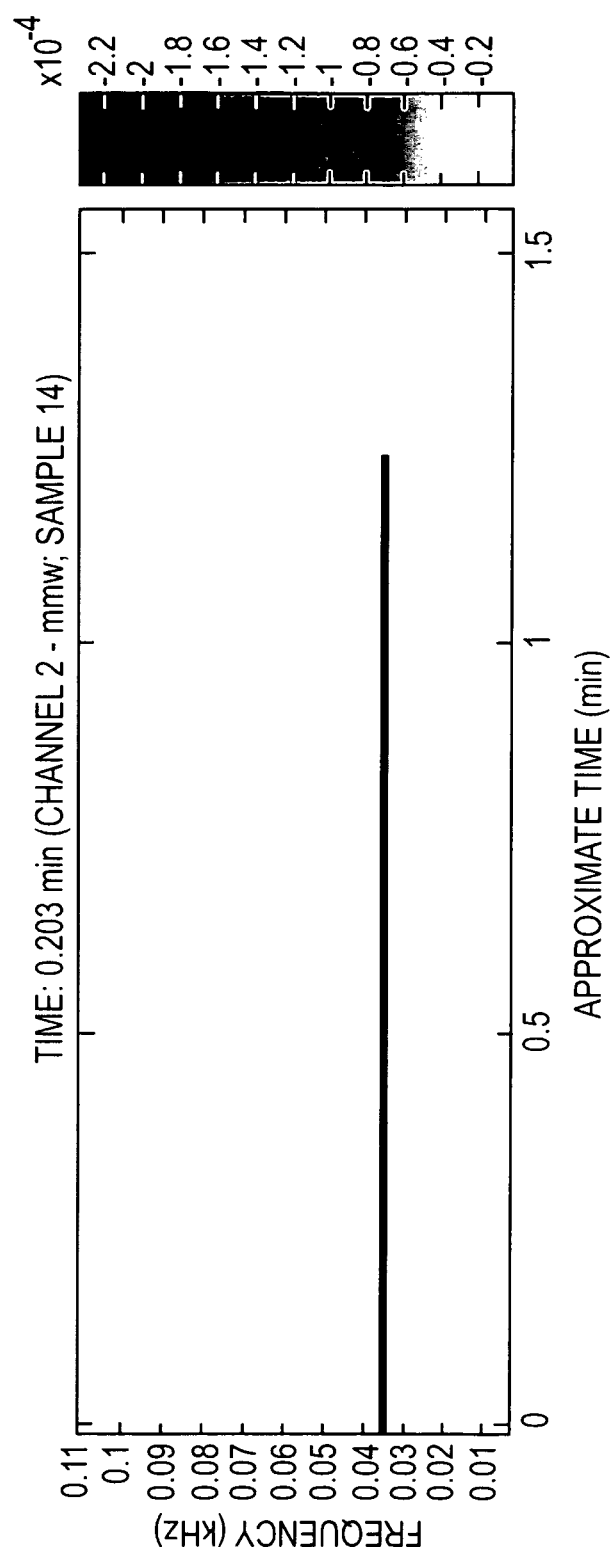

Sensitivity of the MMW system to incidence angle (view angle) was assessed. The incidence angle was varied between 0 and about 35 degrees at a range of about 13.7 m. Additionally, assessment of the range of the MWW system was conducted, varying the standoff distance between the target and the sensor (range) from about 15 m, with a 35° incidence angle, to about 25 m, with an oblique incidence angle of less than about 10°. In this example, the target was excited with a single mode of excitation at 35 Hz. Unlike the optical sensor which requires nearly normal orientation, the MMW system beneficially detected a signal over a wide range of view angles. Further, the MMW system provided clear signals in the tested range. FIG. 6A-6C, for example, illustrates the signal obtained from the MMW system at a range of 25 m. FIG. 6A shows time trace; FIG. 6B shows the power spectrum and FIG. 6C shows frequency time from the MMW system 100. On the other hand, no signal was detected using the laser vibrometer at the 25 m range, and in fact no signal was detected with the laser vibrometer beyond 15 m.

Example 4

Figure 7A:
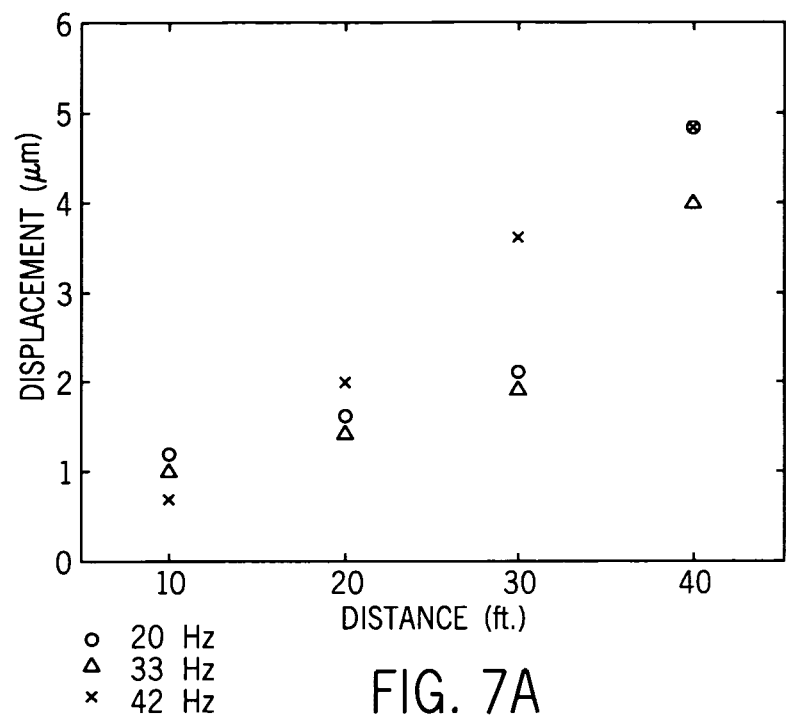
FIG. 7A shows a plot of detectable displacement with the MMW system (maintaining a signal-to-noise ratio (S/N) greater than about 2) as a function of standoff distance from a target at three arbitrarily selected target excitation frequencies.
Figure 7B:
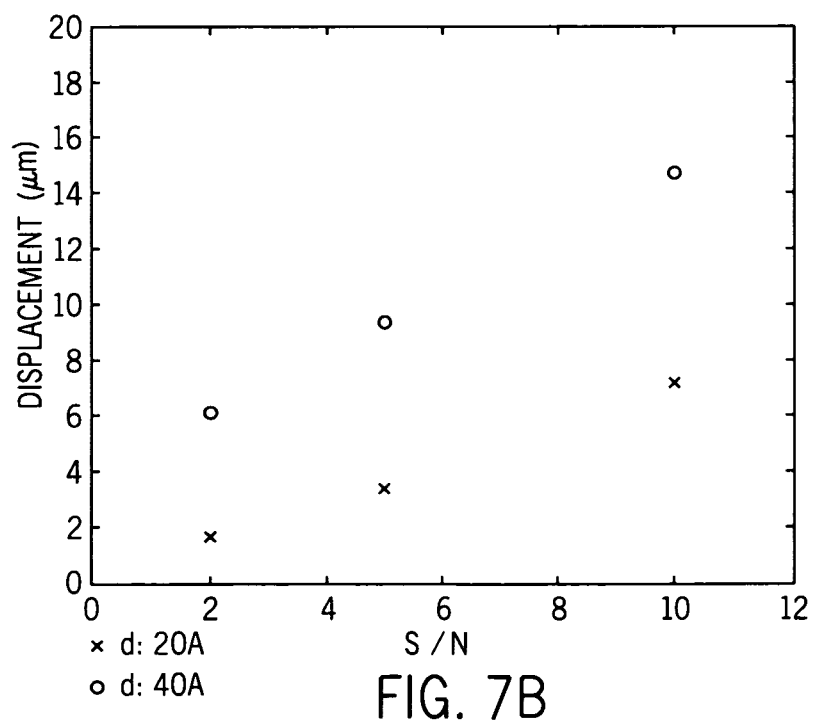
FIG. 7B shows a plot of the target average displacement at multiple excitation frequencies (less than 20 Hz) as a function of S/N at two standoff distances.

A series of tests were conducted to quantitatively assess the sensitivity of the MMW system. Once again, the laser vibrometer readings were used to quantify the displacement of the target, which was done by placing an optical reflector on the target. For the first test, the cinder block target was excited at three arbitrarily selected vibration frequencies and detectable displacement was measured as a function of standoff distance. Detection was based on a minimum signal to noise ratio (S/N) of about 2 at which a clear signal above the background was observable. FIG. 7A shows a plot of the results obtained from the MMW system. For all three vibration frequencies, 20, 33 and 42 Hz, a displacement of less than 5 μm was detectable at the longest standoff distance evaluated, about 15 m. For the second test, the detectable displacement (S/N of about 2) was recorded as a function of S/N at two standoff distances (about 7 m and about 14 m) at various excitation frequencies of the target. FIG. 7B is a plot illustrating the results, where measurement points on the plot represent the average value of readings at multiple vibration frequencies (all less than 20 Hz). The data show that more decisive detections (higher S/N) are made at higher vibration displacements.

Example 5

Evaluation of the MMW system for detection and/or monitoring of human or animal vital signs (biometric sensing) was conducted. First, movements associated with respiration and heartbeat were simulated by using the vibration exciter system described in the Examples above. The surface of the target was covered with a layer of lossy dielectric material (rubber sheet) to simulate reflection from the human body. The arbitrary function generator was used to simulate an exemplary biometric signal composed of a tapered-edge pulse and a sine function that represented the respiration (RR) and heart rate (HR), respectively.

Figure 8A:
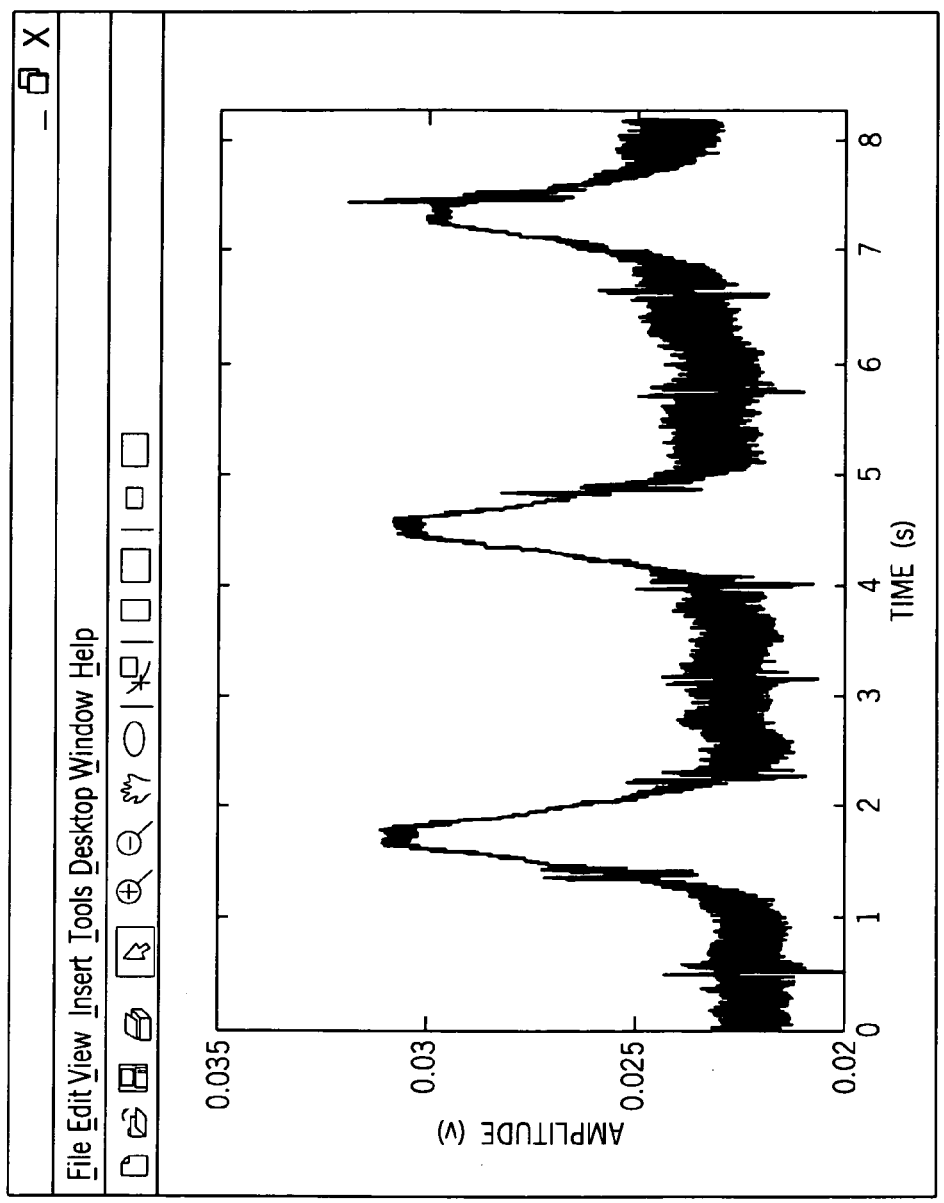
FIG. 8A shows a plot of the time domain signal obtained from the MMW system for a simulated biometric signal composed of a respiration rate of about 0.36 Hz and a heart rate of about 1.1 Hz.
Figure 8B:
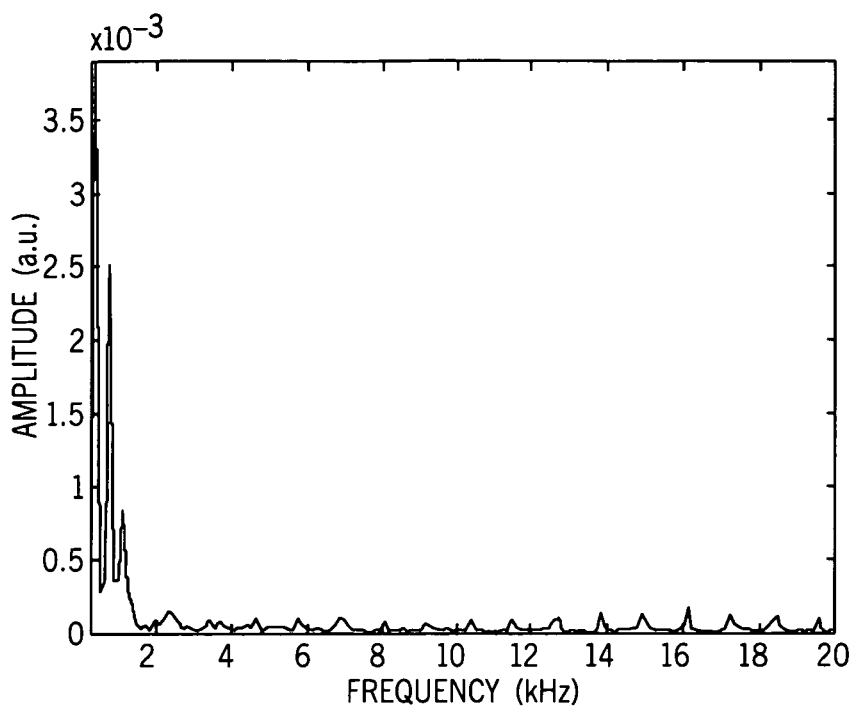
FIG. 8B shows a plot of a portion of the power spectrum of the signal of FIG. 8A.
Figure 8C:
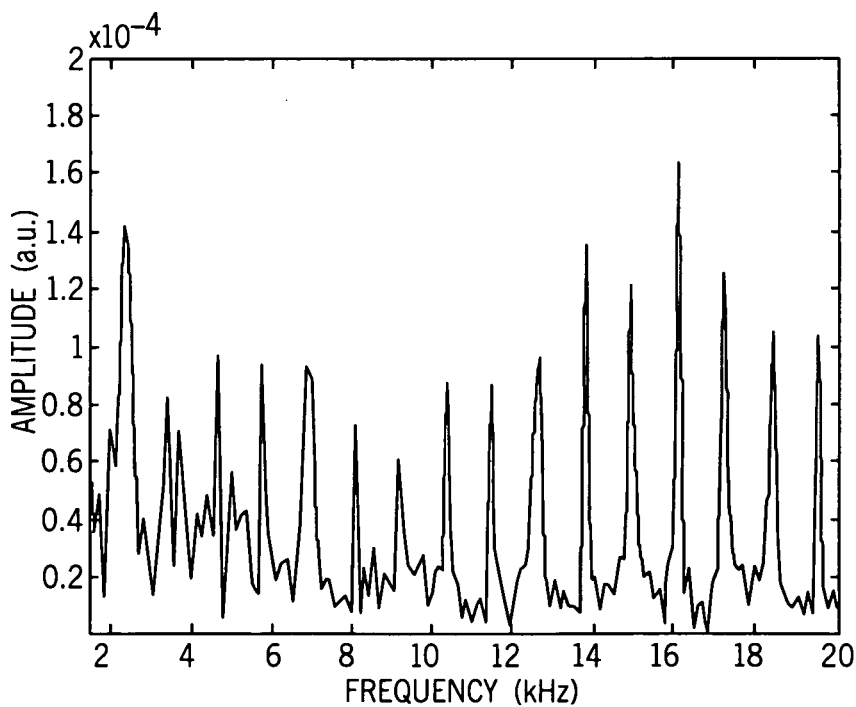
FIG. 8C shows a plot of the power spectrum for frequency components above 2 Hz.

The RR in this case was set to 0.36 Hz and the HR was set to 1.1 Hz (both within the normal range of values reported in the literature). With an optical reflector placed on the target, the laser vibrometer readings, used as a reference, indicated a total displacement of about 0.04 mm for the respiration function and roughly a third of that (0.013 mm) for the heart function. It is worth noting that the simulated displacement is about five times smaller than the typical displacement associated with chest movement due to the respiration function. FIG. 8A shows a plot of the time trace from the MMW sensor output at a short standoff distance (about 5 m) that closely resembles the output of the function generator. Both the RR and the HR signal are clearly visible along the approximately 8 second trace. FIG. 8B shows a portion of the power spectrum of the time-domain data shown in FIG. 8A. The RR and HR fundamental frequencies in FIG. 8B are the dominant components depicted. A portion of the same power spectrum for frequencies above 2 Hz is shown in FIG. 8C. The higher order harmonics of the simulated HR are clearly visible in this plot in FIG. 8C.

Example 6

Figure 9A:
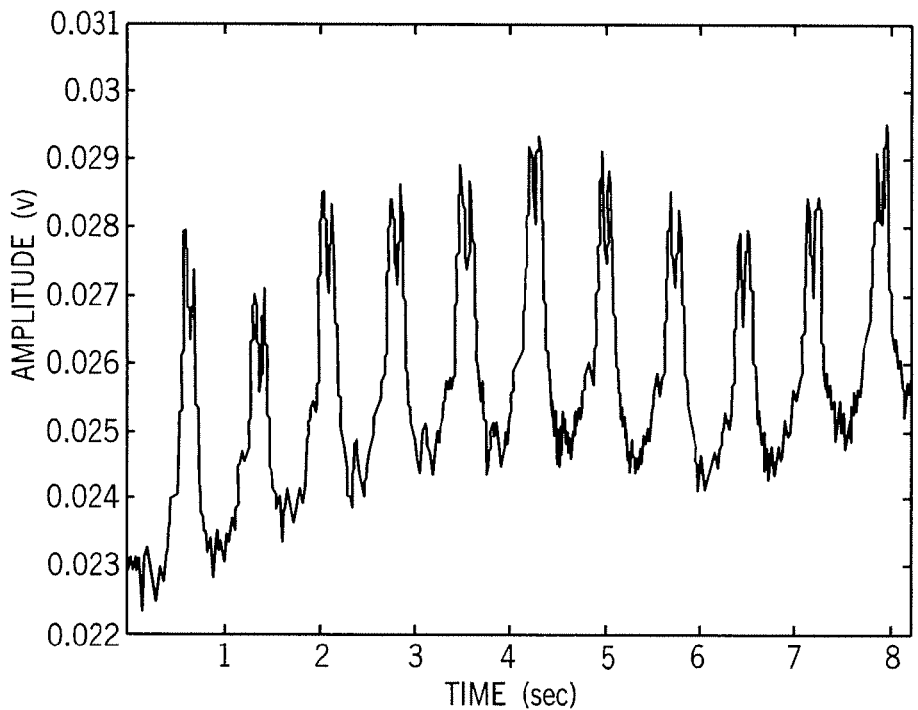
FIGS. 9A and 9B show time domain and power spectrum plots, respectively, of a heartbeat signal obtained using the MMW sensor aimed at the chest region of a human subject at a standoff distance of 10 m.
Figure 9B:
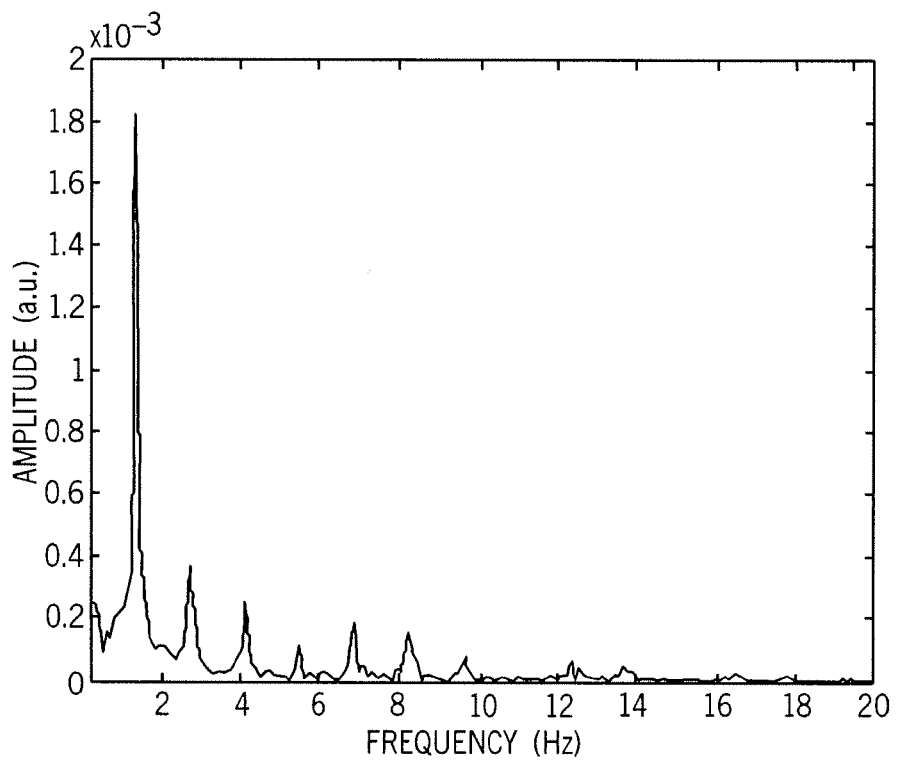

Biometric sensing with the MMW system was also evaluated using a stationary human target. The MMW system collected a response from a stationary human target at a standoff distance of 10 m. The respiration function was suppressed in this test in order to assess the ability of the system to clearly detect the HR signal of the subject. FIG. 9A shows a time plot of the HR signal obtained with the MMW system over an interval of about 8 seconds. The periodic heartbeat signal (HR) is clearly observable in the time trace. The corresponding power spectrum is displayed in FIG. 9B and shows the fundamental frequency and the harmonics of the HR signal.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method for detecting an object characteristic at a remote far field location, comprising the steps of:
   providing a system with a transmitter portion including an oscillator coupled to a power source, the transmitter configured to generate an electromagnetic wave having a wavelength the W-band (75-110 GHz);
   directing the electromagnetic wave toward an object located in the far field;
   focusing the electromagnetic wave via a Gaussian optic lens antenna;
   detecting, via a transceiver, a reflected electromagnetic wave from the object, the transceiver measuring an amplitude and a phase of the reflected electromagnetic wave; and
   processing the amplitude and phase detected by the transceiver to measure displacement of the object.

2. The method of claim 1, further comprising the step of using a filter coupled to the transceiver portion with the filter reducing electromagnetic noise detected by the transceiver.

3. The method of claim 1 wherein the object characteristic includes at least one of object displacement, object velocity, object acceleration, object frequency of displacement and position of the object.

4. The method of claim 1, wherein the displacement detected is less than about 1 micron, thereby enabling detection of an object characteristic selected from the group of human breathing, human heart activity, and human motion on small scale.

5. The method of claim 4, wherein the distance from the transceiver to the object is greater than about 10 meters.

6. The method of claim 1 further providing an antenna size enabling a portable size for the system.

7. The method of claim 1, further providing the step of measuring the object characteristic through intervening materials which do not affect measurability of the electromagnetic wave detected by the transceiver.

8. The method of claim 1, further including a quadrature mixer which measures simultaneously the amplitude and the phase of the reflected electromagnetic wave.

9. The method of claim 1 further including the step of detecting one or more vibration modes of the object.

10. A method for remotely detecting an object's characteristics, comprising:
    providing a remote measurement system separated from the object by a distance sufficient to place the object in the far field, the remote measurement system comprising:
    a transmitter portion generating modulated electromagnetic wave having a W-band wavelength;
    a Gaussian optic lens antenna; and
    a transceiver portion detecting a reflected electromagnetic wave from the object;
    measuring one of Doppler frequency shift and phase modulation induced by the object on the reflected modulated electromagnetic wave;
    processing measured one of Doppler frequency shift and phase modulation to indicate a displacement of the object, thereby providing a sensitivity in the micron displacement range.

11. The method of claim 10, wherein the object is a natural object.

12. The method of claim 10, wherein the displacement is indicative of at least one of a heart rate and a respiration function of the natural object.

13. The method of claim 12, wherein the distance to the natural object is at least about 10 meters.

14. The method of claim 10, further comprising detecting a portion of the reflected electromagnetic wave and storing the reflected component in a memory device for analysis steps.

15. The method of claim 14, further comprising the step of obtaining a power spectrum indicative of the vibrational displacement of the object.

16. A method for remotely detecting a biometric function, comprising:
    providing a natural object;
    providing a remote measurement system, the remote measurement system outputting an electromagnetic wave having a millimeter scale wavelength with frequency between 75-300 GHz, the remote measurement system separated from the natural object by a distance sufficient to place the natural object in the far field and an intervening optically opaque barrier;
    focusing the electromagnetic wave via a Gaussian optic lens antenna;
    directing the electromagnetic wave to the natural object;
    detecting through the optically opaque barrier a portion of the electromagnetic wave reflected by the natural object, wherein micron level resolution is achieved the detected component is indicative of a displacement of the object and the displacement is more than about 2-3 micrometers, thereby enabling highly sensitive measurement of the biometric function.

17. The method of claim 16, wherein the displacement is processed to measure at least one of a heart rate and a respiratory function of the natural object.

18. The method as defined in claim 16 wherein the step of directing the electromagnetic wave to the object includes applying the electromagnetic wave over an angle of incidence between zero and 35° while still measuring the detected component, thereby enabling characterization of the biometric function.

19. The method as defined in claim 16 wherein the step of outputting an electromagnetic wave comprises at least one of a pulsed output and continuous wave output.

* * * * *